United States Patent [19]
Tokarz

[11] Patent Number: 5,207,827
[45] Date of Patent: May 4, 1993

[54] EAR PLUG COMPOSITION

[76] Inventor: Joseph F. Tokarz, 211 Van Ness Ave., Ashland, Oreg. 97520

[21] Appl. No.: 885,683

[22] Filed: May 19, 1992

[51] Int. Cl.$^5$ .............................................. C08L 3/06
[52] U.S. Cl. .................................. 106/212; 128/864; 514/778
[58] Field of Search ....................... 106/212; 128/864; 514/778

[56] References Cited

U.S. PATENT DOCUMENTS

| | | | |
|---|---|---|---|
| 2,574,288 | 11/1951 | Rosenblatt | 128/864 |
| 3,852,475 | 12/1974 | Tarangul | 514/778 |
| 3,928,666 | 12/1975 | Morrison et al. | 106/212 |
| 4,323,694 | 4/1982 | Scala, Jr. | 514/846 |
| 4,397,913 | 8/1983 | Fahey | 106/212 |

*Primary Examiner*—David Brunsman
*Attorney, Agent, or Firm*—John P. Halvonik

[57] ABSTRACT

The invention is a composition especially for ear plugs comprised of a starch based ester of a dicarboxylic acid, lecithin, wax, trace amounts of vitamins A, C, and E and a biocidal amount of grapefruit seed extract. The ear plug composition is especially useful as it retains its elasticity after prolonged use and after being subjected to temperature extremes. The composition is safe, and also kills germs due to biocidal action of grapefruit seed extract among other ingredients.

7 Claims, No Drawings

EAR PLUG COMPOSITION

DISCLOSURE DOCUMENT REFERENCE

A disclosure document dated Nov. 27, 1991 has been filed in the USPTO with Ser. No. of 297,064,

BACKGROUND OF THE INVENTION

The invention relates to the field of earplug compositions, and especially to one that uses natural ingredients, viz.: beeswax, starch, lecithin, vitamins and grapefruit seed extract.

DESCRIPTION OF THE PRIOR ART

While there are ear plug compositions that are known to use natural ingredients, such as wax, none that applicant is aware of have biocidal effect or use emollients to keep the composition tacky and resilient over long periods of time and after exposure to temperature extremes. Prior art earplugs may lose their tackiness after repeated use, i.e. after a few nights of use they tend to pick up dirt and wax and lose resiliency.

SUMMARY OF THE INVENTION

The invention is a composition especially useful for earplugs and comprised of 70% starch based ester of a dicarboxylic acid, 15% lecithin, 15% wax together with trace amounts of vitamins A, C, and E and an effective biocidal amount of grapefruit extract.

It is an object of the invention to provide an ear plug composition with biocidal activity.

Another object of the invention is to provide an ear plug that is comfortable to wear.

Another objective is to provide an ear plug that will retain its resiliency after being subjected to temperature extremes.

Yet another objective is to provide an ear plug that can be used for long periods without loss of tackiness or the ability to plug the ear channel.

Still another objective of the invention is to provide an ear plug that is biodegradable.

Another objective is to provide an ear plug that is non-toxic.

Other objectives of the invention will become apparent to those skilled in the art once the the invention has been shown and described.

DESCRIPTION OF THE PREFERRED EMBODIMENT

The ear plug composition is preferably made of about 14.62% Soya Lecithin, 14.62% yellow Beeswax, 69.51% starch and trace amounts of vitamins A, C, and E and a biocidally effective amount of Grapefruit Seed Extract. Trace amounts of vitamins A, C and E would be on the order of 0.25% each and the Grapefruit Seed Extract would be about 0.5%. All percentages mentioned are by volume.

The starch for the composition should be a starch based ester of a dicarboxylic acid with Aluminum Starch Octenylsuccinate being preferred. This starch derivative is found to work well in the present composition and commonly goes by the tradename of DRY-FLO, a product name of the National Starch Company of Bridgewater, N.J. A U.S. Pat. No. 2,613,206, also covers this starch.

Other starches may of course, be used without violating the spirit of the invention. These may include corn starch, potato, tapioca, rice, waxy maize, arrowroot, kuzu and other similar starches, as well as a number of modified starches. Other water soluble salts of starches could be used, an Aluminum based salt is not exclusive. Other salts may be based on copper, mercury, zirconium, calcium, iron, chromium, tin, barium and strontium.

The preferred wax is refined yellow beeswax but, of course, other waxes could be used without violating the spirit of this invention. Although the invention is primarily directed toward natural ingredients, synthetic waxes could be used without violating the spirit of the invention. The vitamin E is preferably a d-alpha tocopherol with mixed tocopherols (e.g. d-Delta, d-Beta and d-Gamma tocopherols). The preferred vitamin C would in the form of ascorbyl palmitate. The preferred form of vitamin A would be Vitamin A Palmitate.

To make the composition: melt one part refined yellow beeswax and add an equal part liquid soya lecithin and mix. Add grapefruit extract, vitamins A, C, and E. To this composition is added four parts Dry FLO starch (see above). The ingredients are gently mixed over low heat 140°–160° F. until the mixture is smooth and evenly blended.

The ear plug composition may be cooled slowly at room temperature or cooled quickly by exposing to lower temperatures. The resulting composition is of golden color and may be shaped by the hand into earplugs or may be mechanically extruded into the same.

By Grapefruit seed extract it is meant what is commonly referred to as Grapefruit oil and also goes by the synonyms of Shaddock oil, and citrus preservative. The peel oil and seed oil contain monoterpenes, limogene (90%), sesquiterpenes, aldehydes, citronellyl, nootkatone, ketones, bergaptens, 7-methodxy-8-2-formyl-2-methyl propyl, and other substances. See dermatological studies in: D. L. J. Opdyke, *Food Cosmet. Toxicol.* 12, 723, 1974.

The composition is found to be very water resistant, and should be able to remain resistant to wetting even after 12 hours of underwater wear. The composition may remain resistant for even longer periods and these should be more than enough for average use. Body heat will soften the composition slightly when it is placed in the ear opening and this results in an earplug that is very comfortable. In contrast to foam earplugs, those of the present invention do not lose their resiliency or tackiness after repeated use. As such they form a good seal against the ear for long uses. They also have very effective sound-deadening qualities.

I claim:

1. A resilient composition, especially useful for earplugs, comprising: about 1 part by volume wax, 4 parts by volume starch based acid ester of a dicarboxylic acid, 1 part by volume soya lecithin and a biocidally effective amount of grapefruit seed extract.

2. The composition of claim 1 in addition comprising about 0.25% by volume vitamin A.

3. The composition of claim 2 wherein said starch based ester is Aluminum Starch Octenylsuccinate.

4. The composition of claim 1 in addition comprising about 0.25% by volume of vitamin C.

5. The composition of claim 4 wherein said starch based ester is Aluminum Starch Octenylsuccinate.

6. The composition of claim 1 in addition comprising about 0.25% by volume of vitamin E.

7. The composition of claim 6 wherein said starch based ester is Aluminum Starch Octenylsuccinate.

* * * * *